United States Patent [19]

Zoski et al.

[11] Patent Number: 5,061,445

[45] Date of Patent: Oct. 29, 1991

[54] APPARATUS FOR CONDUCTING MEASUREMENTS OF ELECTROCHEMILUMINESCENT PHENOMENA

[75] Inventors: Glenn Zoski, Rockville, Md.; Steve Woodward, Chapel Hill, N.C.

[73] Assignee: Igen, Inc., Rockville, Md.

[21] Appl. No.: 267,234

[22] Filed: Nov. 3, 1988

[51] Int. Cl.[5] .......................................... G01N 21/76
[52] U.S. Cl. .................................. 422/52; 250/361 C; 307/228; 328/181; 328/185; 340/781; 359/85
[58] Field of Search .............. 350/332, 331 R; 422/52; 328/181, 185; 307/228; 340/781; 250/361 C

[56] References Cited

U.S. PATENT DOCUMENTS

| | | | |
|---|---|---|---|
| 3,676,784 | 7/1972 | Le Comte | 328/181 |
| 3,868,534 | 2/1975 | Pighin et al. | |
| 3,961,253 | 6/1976 | Brych | |
| 3,963,928 | 6/1976 | Zolner | 422/52 X |
| 3,984,688 | 10/1976 | Von Bargen et al. | 422/52 X |
| 4,204,037 | 5/1980 | Dill et al. | |
| 4,236,895 | 12/1980 | Stahl | |
| 4,280,815 | 7/1981 | Oberhardt et al. | |
| 4,303,410 | 12/1981 | Copeland | 250/361 C |
| 4,431,919 | 2/1984 | Kostlin et al. | |
| 4,634,574 | 1/1987 | Spurlin et al. | 422/52 |
| 4,689,305 | 8/1987 | Stiffey et al. | 422/52 X |
| 4,721,601 | 1/1988 | Wrighton et al. | |
| 4,818,883 | 4/1989 | Anderson et al. | 422/52 X |
| 4,822,564 | 4/1989 | Howard | 422/52 |

FOREIGN PATENT DOCUMENTS 1247962 11/1986 Japan .................................... 422/52
86/2734 5/1986 World Int. Prop. O. .

OTHER PUBLICATIONS

*Electrochemical Luminescence-Based Homogeneous Immuno-Assay*, Biochemical and Biophysical Research Communications, Ikariyama et al., vol. 128, No. 2, Apr. 1985, pp. 987–992.

Y. Ikariyama et al., Biochemical and Biophysical Research Comm., vol. 128, No. 2, pp. 987–992, 4/30/85.

Primary Examiner—Robert J. Warden
Assistant Examiner—Amalia L. Santiago
Attorney, Agent, or Firm—Barry Evans

[57] ABSTRACT

An apparatus for conducting measurements of electrochemiluminescent (ECL) phenomena includes a cell unit having an electrode configuration for inducing the emission of ECL light by the application of a selected voltage waveform to a sample fluid including an ECL moiety. The sample fluid is transported to and from the cell unit by a flow-through pump/tubing system. A photomultiplier tube detects the intensity of light emitted by the sample fluid during the ECL measurement process. A computer control unit both analyzes the detected data and provides digital control signals to the cell unit to generate effective voltage waveforms. The digital control signals are supplied to a novel pulse width modulated digital to analog converter which outputs a ramp voltage waveform having the desired slope.

22 Claims, 7 Drawing Sheets

APPARATUS FOR CONDUCTING MEASUREMENTS OF ELECTROCHEMILUMINESCENT PHENOMENA

FIELD OF THE INVENTION

The present invention relates to apparatus for conducting measurements of electrochemiluminescent phenomena and more particularly is directed to apparatus which applies effective voltage waveforms to induce an electrochemiluminescent moiety to repeatedly emit electromagnetic radiation.

BACKGROUND OF THE INVENTION

Electrochemiluminescent (ECL) measurement techniques derive from electrochemistry and chemiluminescent detection techniques. Electrochemistry deals generally with the relation of electricity to chemical changes and with the interconversion of chemical and electrical energy, while chemiluminescence deals generally with the chemical stimulation of luminescence, i.e., the emission of light by a mechanism other than incandescence, and includes techniques for identifying the presence and/or concentration of an analyte of interest.

ECL techniques are also useful in the detection and measurement of analytes of interest. For example, in a binding assay methodology, a mixture is formed of a sample containing an unknown amount of an analyte of interest to be determined and a known amount of a reactant which is conjugated with an ECL label. The mixture is incubated to allow the labeled reactant to bind to the analyte. After incubation, the mixture is separated into two fractions: a bound and an unbound fraction. The bound fraction is labeled reactant bound to analyte and the unbound fraction is the remaining unbound reactant. The incubated sample is then exposed to a voltammetric working electrode, that is, an electrode to which a voltage waveform is applied and from which a current from a redox reaction may be passed. The voltage waveform is selected to apply electrical energy to the sample at a particular time and in a particular manner to cause the sample to react with both its chemical environment and the applied electrical energy so as to be triggered to repeatedly emit electromagnetic radiation. Advantageously, the wavelength of the emitted radiation will be in the visible spectrum, i.e., visible light is emitted, and the ECL measurement of interest is the intensity of this light. In the particular example of a binding assay, the bound and unbound fractions of the labeled reactant will emit different amounts of light at a known wavelength, with the bound fraction generally emitting no ECL light at all. The measured intensity at the known wavelength is indicative of the amount of the bound and/or unbound fraction, respectively, and from such measurements one skilled in the art can determine the amount of analyte in the sample.

It will be understood that many different methodologies may be used to produce the ECL sample and that many different analyses may be performed on the measured light intensities at various wavelengths to detect, measure and identify the analytes of interest. The present invention is not directed to these preliminary or final steps, but rather is directed to the intermediate step of inducing and detecting the ECL radiation and more particularly is directed to an advantageous computer-controlled instrument for this purpose. Other aspects of ECL techniques relating to the preliminary and final steps are discussed in U.S. Pat. Application Ser. No. 07/188,258, filed April 29, 1988 and PCT Patent Application No. US87/00987. The disclosures of these two applications are incorporated herein.

An apparatus for conducting measurements of ECL phenomena must meet precise specifications in its operation. It has been found that even small variations in how the sample is brought into the apparatus, in the state of the voltammetric electrode, or in the applied voltage waveform can result in variations in the induced ECL light intensity which are too large to neglect In particular, it has been found that known ECL moieties react sensitively to the voltage waveforms, and distinguish between constant voltages, ramps, steps and other shapes Indeed, these ECL moieties react to even small variations within the waveforms. As a result, the conventional approximation of a ramp voltage waveform with a digitally generated staircase voltage waveform, i.e., a series of voltage steps, has been found by the present assignee to be ineffective unless the steps are extremely fine. Otherwise, the individual constant voltages and steps are detected by the ECL moieties, which produce light intensities different from those produced in response to a true ramp voltage waveform Although conventional fine staircase generators are commercially available, they are very expensive.

OBJECTS AND SUMMARY OF THE INVENTION

Accordingly, it is an object of the present invention to provide apparatus for conducting measurements of electrochemiluminescent phenomena which avoids the above-described difficulties of the prior art.

It is another object of the present invention to provide apparatus for conducting measurements of electrochemiluminescent phenomena which induces and measures ECL light intensities in an accurate and precise fashion.

It is another object of the present invention to provide apparatus for conducting measurements of electrochemiluminescent phenomena which can apply effective voltage waveforms to the voltammetric electrode used to induce the repeated emission of electromagnetic radiation.

It is yet another object of the present invention to provide computer controlled apparatus for conducting measurements of electrochemiluminescent phenomena.

It is still another object of the present invention to provide flow-through apparatus for conducting measurements of electrochemiluminescent phenomena.

It is a further object of the present invention to provide apparatus for conducting measurements of electrochemiluminescent phenomena which includes a ramp voltage waveform generator which generates an effective ramp voltage waveform.

It is yet a further object of the present invention to provide such apparatus for conducting measurements of electrochemiluminescent phenomena wherein the ramp voltage waveform generator is of low cost and simple construction.

It is still a further object of the present invention to provide such apparatus for conducting measurements of electrochemiluminescent phenomena including a pulse width modulated ramp digital to analog converter for generating a ramp voltage waveform.

It is yet a further object of the present invention to provide a method for programmably generating a ramp voltage waveform from a pulse width modulated pulse train.

In accordance with an aspect of the present invention, apparatus for conducting measurements of electrochemiluminescent phenomena comprises cell means for holding a sample fluid which contains an ECL moiety, the cell means including working electrode means mounted for exposure to the sample fluid within the cell means for supplying electrochemical energy to the sample fluid so as to induce the same to repeatedly emit electromagnetic radiation, detector means for detecting electromagnetic radiation emitted by the fluid and providing a signal indicative of the intensity of emitted radiation, control means for generating a digital control signal indicative of a ramp voltage waveform having a selected slope, pulse width modulated ramp digital to analog converter means for generating the ramp voltage waveform in response to the digital control signal and means for applying the ramp voltage waveform across the working electrode means.

In accordance with this aspect of the present invention, the pulse width modulated ramp digital to analog converter means includes programmable timer means for providing a first pulse width modulated pulse train in response to the first digital control signal indicative of the ramp voltage waveform, first and second voltage sources defining upper and lower pulse amplitudes, respectively, multiplexer means connected to the first and second voltage sources and responsive to the first pulse width modulated pulse train for providing a second pulse width modulated pulse train having the upper and lower pulse amplitudes, and integrator means for integrating the second pulse width modulated pulse train and providing the ramp waveform as an output.

In other aspects, the control means advantageously includes a computer, such as a personal computer, and may generate a second digital control signal indicative of a second voltage waveform composed of at least one constant voltage. The apparatus then includes a digital-to-analog converter for generating the second voltage waveform in response to the second digital control signal. The apparatus advantageously includes fluid transport means for transporting the sample fluid to and from the cell.

In accordance with a further aspect of the present invention, a method for generating a pulse width modulated ramp voltage waveform comprises the steps of generating a digital control signal indicative of a selected ramp voltage waveform, generating a pulse width modulated pulse train in response to the digital control signal, and integrating the pulse width modulated pulse train.

The "ECL moiety" is sometimes referred to as a "label", "label compound", "label substance", etc. It is within the scope of the invention for the species termed "ECL moiety"— when utilized in certain embodiments in accordance with the invention - to be linked to other molecules such as an analyte or an analog thereof, a binding partner of the analyte or an analog thereof, a further binding partner of such aforementioned binding partner, or a reactive component capable of binding with the analyte, an analog thereof or a binding partner as mentioned above. The above-mentioned species can also be linked to a combination of one or more binding partners and/or one or more reactive components. Additionally, the aforementioned species can also be linked to an analyte or its analog bound to a binding partner, a reactive component, or a combination of one or more binding partners and/or one or more reactive components. It is also within the scope of the invention for a plurality of the aforementioned species to be bound directly, or through other molecules as discussed above, to an analyte or its analog.

It is similarly within the scope of the invention for the aforementioned "fluid" to contain metastable and other intermediate species formed in the course of the ECL reaction, such as an ECL moiety in an excited state as aforesaid and the above-mentioned strong reducing agent.

Additionally, although the emission of visible light is an advantageous feature of certain embodiments of the invention it is within the scope of the invention for the fluid to emit other types of electromagnetic radiation, such as infrared or ultraviolet light, X-rays, microwaves, etc. Use of the terms "electrochemiluminescence", "electrochemiluminescent", "electrochemiluminesce", "luminescence", "luminescent" and "luminesce" in connection with the present invention does not require that the emission be light, but admits of the emission's being such other forms of electromagnetic radiation.

These and other objects, aspects and features of the present invention will become apparent from the following detailed description of a preferred embodiment thereof taken in connection with the accompanying drawings, throughout which like reference numerals denote like elements and parts.

DETAILED DESCRIPTION OF THE PREFERRED EMBODIMENT

Figure 1:
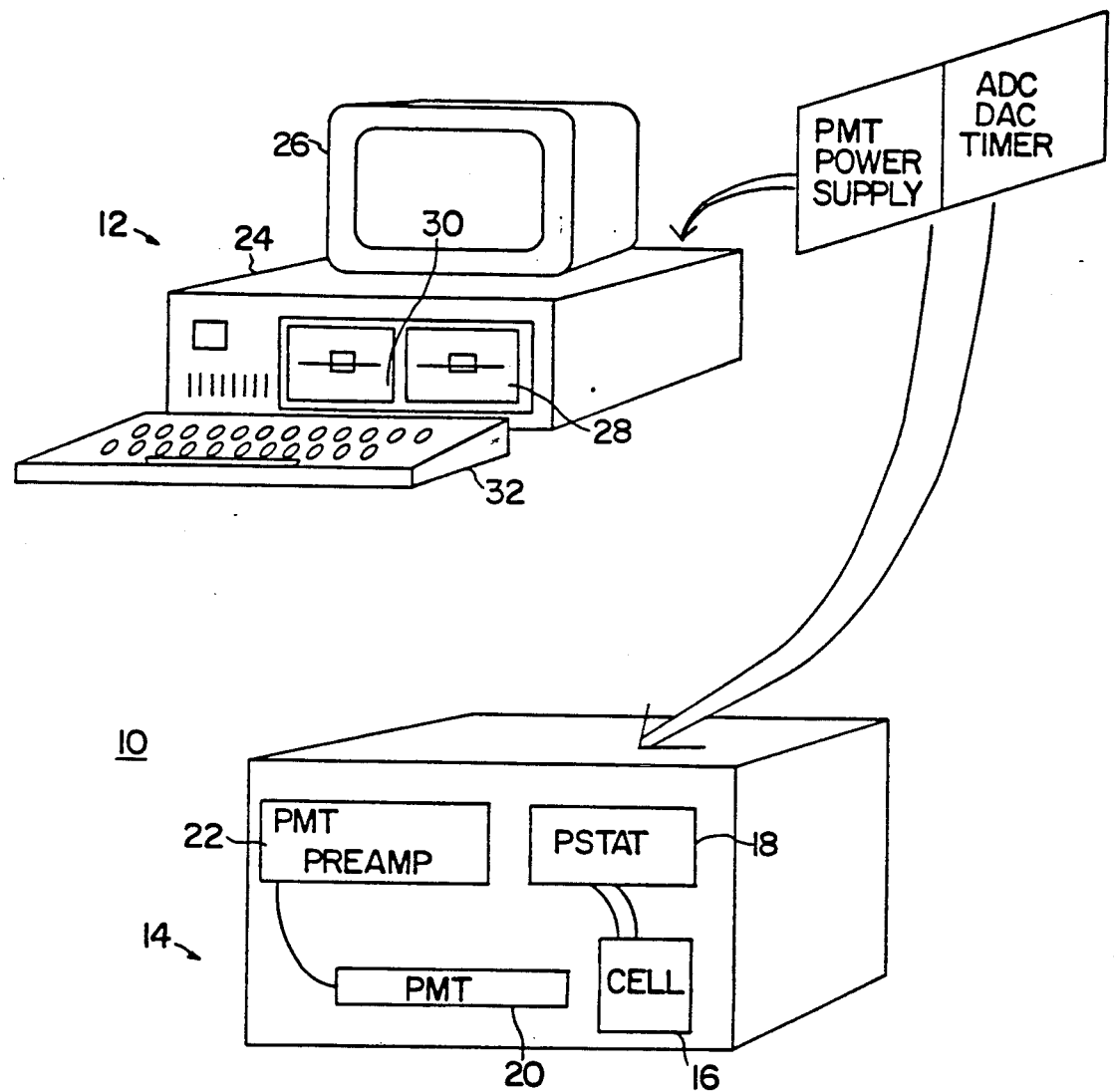
FIG. 1 is a schematic illustration of a preferred embodiment of the apparatus for conducting measurements of electrochemiluminescent phenomena in accordance with the present invention.

Turning now to the drawings and initially to FIG. 1 thereof, an apparatus 10 for conducting measurements of ECL phenomena in accordance with the present invention includes a computer control unit 12 and a cell unit 14 connected together for communication over a cable (not illustrated). Cell unit 14 includes an ECL cell 16 in which the sample fluid including the ECL moiety is held during the measurement process. A suitable cell configuration is disclosed in copending Massey et al. application Ser. No. 266,882 filed on even date herewith entitled ("Microparticulate-Based Nonseparation Binding Assay"), the contents of which are incorporated by reference. The ECL sample is transported to and from ECL cell 16 via a pump/tubing arrangement discussed in greater detail below.

Cell 16 itself includes an electrode configuration for inducing the ECL sample to repeatedly emit electromagnetic radiation at a wavelength in the visible spectrum, the particular wavelength being dependent on the characteristics of the ECL moiety. Such an electrode configuration conventionally includes a voltammetric working electrode, a counter electrode and optionally a reference electrode. Cell unit 14 further includes a potentiostat 18 for generating and applying any of a number of voltage waveforms to the electrode configuration. In a three electrode mode of operation, potentiostat 18 maintains a potential between the working and counter electrodes equal to the desired voltage waveform so as to induce the ECL moiety to emit light, while the reference electrode provides a reference potential to measure the working electrode potential against. In a two electrode mode, the counter electrode serves as both counter and reference electrode.

The light generated within cell 16 is detected by an appropriate light detector, here a photomultiplier tube (PMT) 20 within cell unit 14. Other light detectors, for example photodiodes, may also be used. Each individual ECL moiety molecule will be induced to repeatedly emit individual photons of light which are detected by PMT 20 to measure the intensity of light emitted. PMT 20 is controlled by PMT preamplifier stage 22 which is designed to allow simultaneous analog and pulse counting outputs from PMT 20, as will be described in more detail below.

Control unit 12 includes a computer control 24, advantageously in the form of a personal computer including a CRT 26, disk drives 28, 30 and keyboard 32. Keyboard 32 is used to enter the operator's commands, to program a sequence of steps for conducting an ECL measurement and for the development of data manipulation and instrument calibration algorithms. Control unit 12 may be used to control the PMT voltage through PMT preamplifier 22 and also supplies one or more digital control signals to determine the particular voltage waveform which will be applied to the electrode configuration in cell 16. Control unit 12 may be programmed to automatically conduct measurement-/calibration cycles independent of the operator, and may also be programmed for interactive operation during the measurement/calibration cycles. In particular, a desired ramp waveform having a desired slope and duration may be programmably generated in response to a digital control signal from control unit 12.

Figure 2:
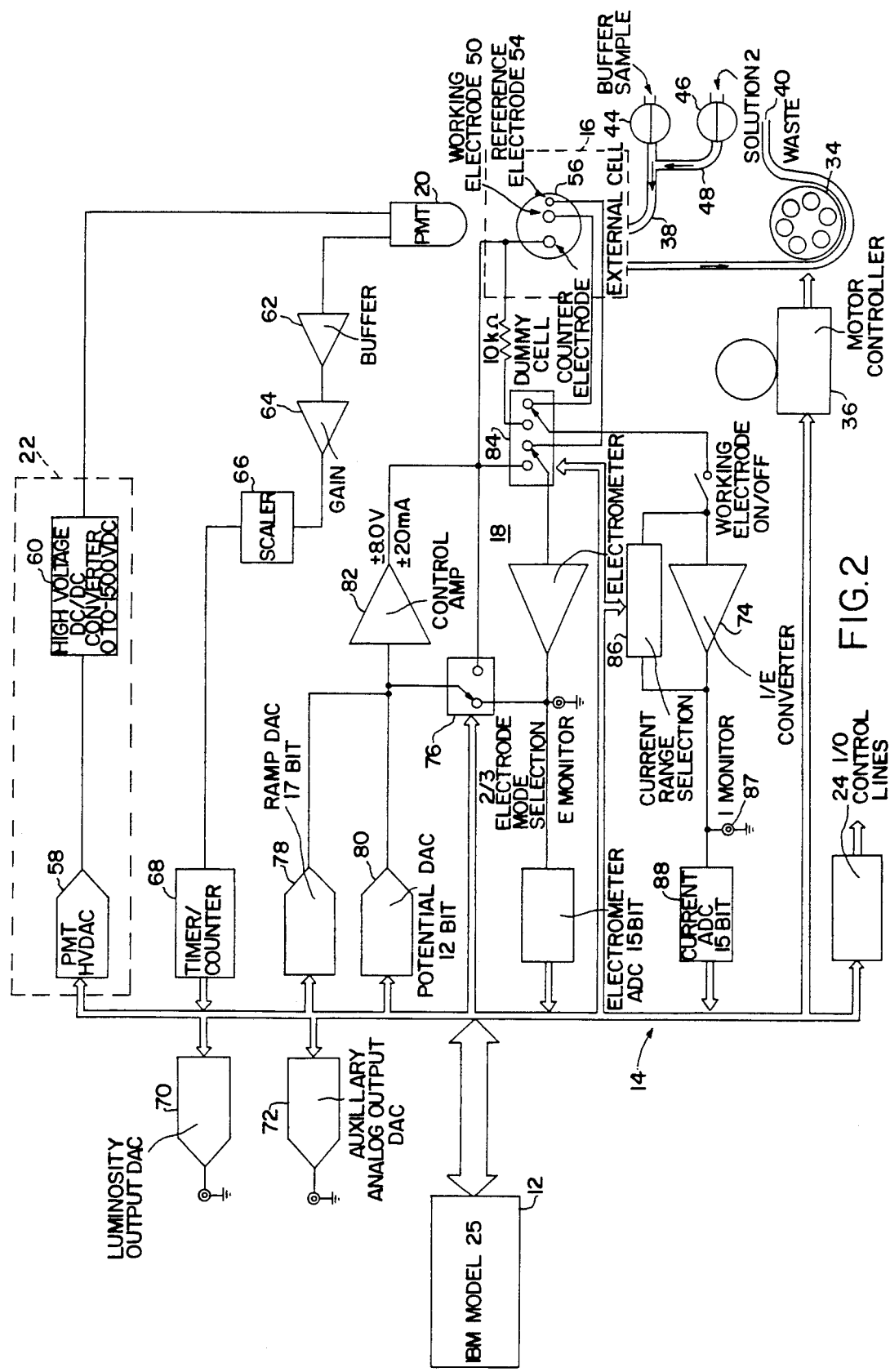
FIG. 2 is a block diagram of the apparatus of FIG. 1.

FIG. 2 provides a more detailed illustration of apparatus 10. Control unit 12 communicates with cell unit 14 in both directions over an RS232 cable, transmitting commands to control the supply of sample fluid or other fluid to and from cell unit 12 and to control the mode of operation of potentiostat 18 and the electrode configuration within cell 16. Turning first to the mechanism for transporting the sample and other fluids to and from cell 16, it will be seen that this mechanism includes a pump 34 including a motor (not illustrated), a motor controller 36 for controlling the speed and direction of the motor within pump 34, inlet tubing 38 and outlet tubing 40. Both the inlet and outlet tubing 38, 40 may be advantageously constructed of stainless steel or plastic. The sample solution is supplied through inlet tubing 38 to cell 16 through a first valve 44 which is opened and closed in response to commands received from control unit 12. As is described in the above-referenced, patent application Ser. No. 07/188,258, other solutions beside the sample solution are advantageously used in apparatus 10 to provide calibration/reference measurements for the sample measurements. In particular, the sample is advantageously provided in a buffer solution, which itself may be ECL active. This buffer solution is also supplied through first valve 44 to cell 16. This has the advantage that when the buffer solution is passed through valve 44 and inlet tubing 38, it washes the inner surfaces of these elements to remove any remaining sample solution which may cling to these inner surfaces and which may contaminate a next input sample solution.

A second valve 46 is also provided with auxiliary input tubing 48 for suppling a second solution to cell 16. Again, the buffer solution for the second sample solution may be fed through second valve 46 to clean the inner surfaces of second valve 46 and auxiliary tubing 48. Second valve 46 is also opened and closed in response to signals from control unit 12. Motor controller 36, pump 34, valves 44 and 46 and tubing 38, 40, 48 are all held on a motor/logic board, which may include an ancillary power supply.

As mentioned above, cell 16 includes a working voltammetric electrode 50, a counter electrode 52 and a reference electrode 54. The ECL sample is held within cell 16 in a sample holding volume 56, and working, counter and reference working electrodes 50–54 are all in contact with the fluid within sample holding volume 56 so as to establish the appropriate potentials within and across the sample fluid which trigger the emission of the ECL light. During the ECL measurement process, the important chemical reactions which generate light in the presence of the impressed electrical energy occur at the surface of working electrode 50. The applied voltage waveforms referred to herein are the voltages appearing at the working electrode 50 with respect to the reference electrode 54. Reference electrode 54 may be, for example, an Ag/AgCl reference electrode.

Inlet tubing 38, sample holding volume 56 and outlet tubing 40 comprise a single flow-through path for bringing the solutions into and out of cell 16 under the control of control unit 12. This is advantageous, in that the electrode configuration may be precisely controlled both during the measurement operation and during any preliminary cleaning/conditioning steps while being continuously in the presence of a solution and without being exposed to air. This also permits the transport of a number of different solutions into and out of cell 16, using appropriate buffer solutions to wash the interior surfaces of the flow-through path and without requiring the disassembly of any part of apparatus 10. Such disassembly would be required, for instance, if cell 16 were constructed to hold the sample solution therein and to be replaceable for each measurement. Although such replaceable cells are useable in apparatus 10 in accordance with the present invention, it is currently believed that the flow-through construction illustrated in FIG. 2 is advantageous for the above-mentioned reasons.

One surface of sample holding volume 56 is covered with a clear glass or plastic cover (not illustrated) through which the photons emitted during the ECL triggered process pass to a detection surface of PMT 20. This detection surface of PMT 20 includes a filter (not illustrated) which transmits only those photons corresponding to the known wavelength of light emitted by the particular ECL moiety within sample holding volume 56 and currently being measured.

The operating voltage of PMT 20 is established, again through commands from control unit 12, through the preamplifier stage 22 including PMT high voltage digital to analog (HVDAC) converter 58 and high voltage DC/DC converter 60. HVDAC converter 58 is a pulse width modulated DAC in accordance with the present invention and it and converter 60 will be discussed in greater detail below. The output from PMT 20, which is indicative of the number of detected photons at the particular known wavelength emitted during the ECL triggering process, is transmitted through a video amplifier buffer 62, a video gain amplifier, a scaler circuit 66 and a timer/counter 68. As is well known, PMT 20 produces pulses in response to the received photons, with the number of pulses produced being directly related to, although not precisely equal to, the number of photons. Each of these pulses is approximately 10–20 nanoseconds wide, although ideally each pulse is infinitesimally wide. The gain of a standard PMT is approximately $10^6$ or $10^7$ per measurable photon. However, at room temperature, PMT 20 will produce spurious pulses generated in response to thermally released electrons within PMT 20 itself. PMT 20 can be cooled in order to inhibit such thermally released electrons, but this is disadvantageous because PMT 20 is advantageously positioned as close as possible to the transparent cover of sample holding volume 56. Cooling PMT 20 would therefore result in cooling of the sample fluid and working electrode 50, which would then result in a changed intensity of triggered ECL radiation. The spurious pulses from the thermally released electrons sometimes have amplitudes lower than the amplitudes of the pulses from the photon released electrons, and so the spurious pulses can be discriminated against in the process of pulse counting by using a device whose input includes a thresholding circuit. A CMOS flip-flop circuit provides this thresholding circuit and is also used as a scaling function to divide the number of pulses by four. The division by four is advantageous in increasing the dynamic range of apparatus 10. Therefore, to reduce the effects of the spurious pulses, the number of pulses is divided by four in flip-flop circuit 66, which may be two D flip-flops in series.

Timer/counter 68 receives the output of flip-flop circuit 66 and performs two functions. First, it counts each pulse output from flip-flop circuit 66, or in other words every fourth pulse from PMT 20. Secondly, timer/counter 68 also counts every eighth pulse from flip-flop circuit 66 which is every 32nd pulse from PMT 20. Using these fractional numbers of photons increases the dynamic range of apparatus 10 when the light intensity is high. If the light intensity is low, it is better to count each photon digitally in order to provide a correct estimate of the intensity. To reduce the effect of thermally released electrons, or to increase the dynamic range, counting each fourth pulse from PMT 20 will provide an accurate measure of the intensity. If counting every fourth pulse still results in excessively high counts per unit time, a count of each 32nd pulse is believed to provide sufficient precision under many circumstances. However, if it appears that counting only every 32nd pulse is necessary, then it has been found that there are enough photons, as opposed to pulses, so that in fact the pulses should be regarded as forming an analog current and analog methods should be used to measure such a standard current. It is known that the dark current produced by the thermally released electrons is in the nanoampere region, but when the number of photons produces a current at 10–100 microamperes, the dark current is negligible. Even at one microampere, the dark current is only 10% of the total, and therefore conventional analog devices may be used to measure the current accurately.

Counter/timer 68 provides its output to luminosity output digital to analog converter (DAC) 70 and to auxiliary analog output (DAC) 72. Luminosity output DAC 70 generates a display, for example a voltage, which is proportional to the count of photons per unit time. Auxiliary analog output DAC 72 may display other types of information, for example the output from I/E converter 74, discussed below. Alternatively, both DACs 70, 72 may be used for post-measurement manipulation of data transmitted from control unit 12 to the two displays.

The voltage waveform applied across electrode 50 and counter electrode 52 is controlled from control unit 12. First, control unit 12 transmits a control signal to two/three electrode mode selection circuit 76 to select one of the two or three electrode modes described above. Secondly, control unit 12 generates a digital control signal which is indicative of a voltage waveform to be applied across the electrode configuration in the two or three electrode mode. A first such digital control signal is indicative of a ramp voltage waveform having a selected slope, and this first digital control signal is supplied to ramp DAC 78. Ramp DAC 78 is responsive to the first digital control signal to generate the ramp voltage waveform having the selected slope. In accordance with an aspect of the present invention, ramp DAC 78, together with PMT HVDAC 58, luminosity output DAC 70 and auxiliary analog output DAC 72 are all pulse width modulated digital to analog converters which produce their output signal in accordance with a novel and advantageous pulse width modulation scheme described below.

Control unit 12 is also adapted to generate a second digital control signal which is indicative of a second voltage waveform advantageously composed of at least one constant voltage. The second digital control signal is supplied to potential DAC 80 and the second voltage waveform is output therefrom. This second voltage waveform is essentially any arbitrary waveform and may consist of only the single constant voltage, a step waveform consisting of several different constant voltages or it may be a pulse waveform varying in a regular manner between know constant voltages. It will be understood that any waveform of any arbitrary shape may be synthesized by the combination of a ramp voltage waveform produced in response to a first digital control signal and the second voltage waveform produced in response to a second digital control signal. Even a curved waveform, such as a sinusoidal waveform, may be synthesized provided the times and values of the particular voltage waveforms are appropriately selected. By using control unit 12 incorporating a personal computer, any arbitrary waveform may be synthesized by the selection and timing of the digital control signals.

Both the ramp and second voltage waveforms, of which only one will generally appear at any one time, although it is possible to superimpose the two, are supplied through a control amplifier 82 to switching circuit 84 which is opened and closed to apply the two waveforms between working electrode 50 and counter electrode 52.

PMT HVDAC 58 is responsive to the commands from control unit 12 to produce a control voltage in the range of 0 to 12 volts. High voltage DC/DC converter 60 is responsive to the 0–12 volt input to produce a 0–1500 volt DC output which is supplied to PMT 20 as its control voltage. As discussed below, PMT HVDAC is programmable over its range to one part in 1500, so that PMT 20 is controllable with a resolution of 1 volt.

Although the usual measurement of interest in ECL is the light intensity, voltammetric working electrode 50 also carries a current generated by the ECL chemical reaction. This current, which is one of the normal measurements of interest in electrochemical techniques, is less relevant in the present environment in which the choice of voltage waveform and electrode configuration are specifically designed to enhance the light emitting properties of the ECL moiety under stimulation from the applied voltage waveform. However, the current measurement may still produce useful information as to, for example, the operating characteristics of the system. Therefore, the current produced at working electrode 50 is transmitted through I/E converter 74 under the control of current range selection circuit 86. Current range selection circuit 86 is also controlled in response to control signals from control unit 12 for precision over the expected current range. The current output from I/E converter 74 may be monitored directly in a current monitor 87 and may also be converted to a digital signal in a current analog to digital converter 88. This data is provided to control unit 12 and, optionally, to auxiliary analog output DAC 72 for display.

Figure 3:
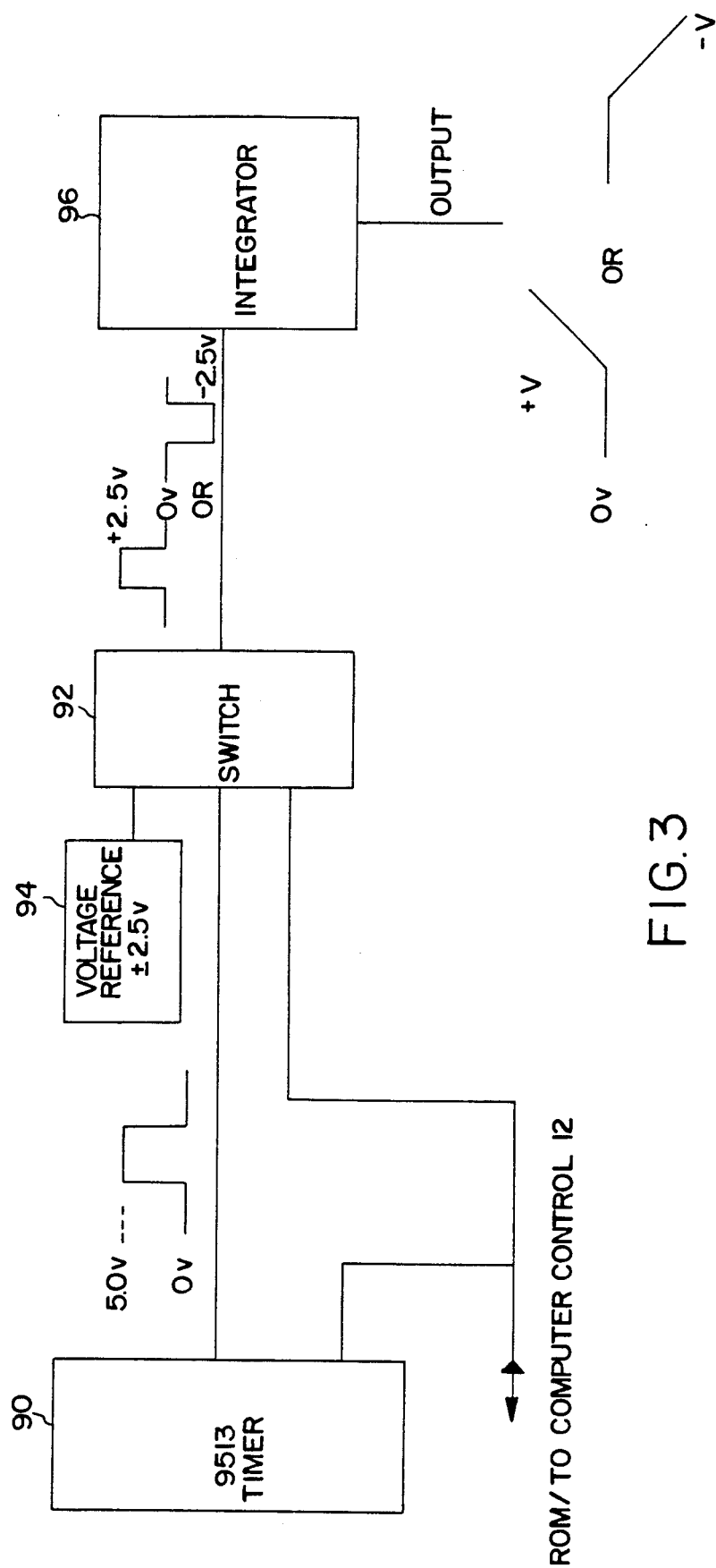
FIG. 3 is a schematic diagram of a preferred embodiment of a pulse width modulated digital to analog converter in the apparatus of FIG. 2.

As mentioned above, four DACs in apparatus 10 operate on a pulse width modulated digital-to-analog conversion method in accordance with the present invention. The basic concept of the programmable pulse width modulated ramp DAC 78 is illustrated in FIG. 3. A programmable timer 90, advantageously a TTL 9513 timer, produces a first pulse train which is pulse width modulated in response to the first digital control signal indicative of the desired ramp voltage waveform More particularly, two values set by the first digital control signal determine the slope of the ramp voltage waveform, which continues until a new digital control signal is received from control unit 12. In the illustrated embodiment, timer 90 is a IC chip which operates between upper and lower voltages, which in TTL logic are +5.0 volts and 0 volts, respectively. The pulse train therefore includes pulses between these upper and lower operating voltages. However, the width of each pulse, i.e., its duty cycle, is determined by the programming of timer 90 in response to the first digital control signal from control unit 12. In order to accurately establish selected upper and lower voltages, the first pulse train from timer 90 is fed to a switch 92 which is connected to upper and lower reference voltage sources. In the illustrated embodiment, these upper and lower reference voltages are +2.5 volts and −2.5 volts, respectively, and in general they are usually of opposite polarity if not exactly symmetrical about zero. The first pulse train is used as a clock to switch the output of switch 92 in response to a third value in the first digital control signal indicating an increasing or decreasing ramp to produce a second pulse train which varies between +2.5 volts and 0 volts or between 0 volts and −2.5 volts, depending on whether the desired ramp voltage waveform is an increasing ramp waveform or a decreasing ramp waveform, respectively. This second pulse train is pulse width modulated in exactly the same manner as the first pulse train. Only the upper and lower levels of the pulses have been changed. The second pulse train is supplied to an integrator 96 which integrates the pulses. Because the increment to the output of integrator 96 in response to each pulse is a DC increment dependent upon the duty cycle of that pulse, the output of integrator 96 is a step-wise ramp voltage waveform having an overall slope determined by the ratio of the duty cycle times the maximum (or minimum) values set by the reference voltages. Said increment is resolved to 1uV corresponding to the 16 bit capacity of the load register. The sweep range of the integrator 96 exceeds 4.096 volts at the potentiostat 18. The effective resolution of the generated analog ramp is therefore one part in 8,192,000 or 23 bits.

The 9513 timer 90 includes a hold register 98 for storing a HOLD value and a load register 100 for storing a LOAD value. Both the LOAD and HOLD values are programmable, and the first digital control signal includes these two values and instructions to timer 90 to store them in hold register 98 and load register 100, respectively. Generation of the first pulse train with the precise duty ratio is achieved by operating the 9513 timer 90 in its so-called mode J in which it runs continuously in a two phase cycle. The duration of one phase is equal to the reference clock, which here is 4.77MHz, divided by the LOAD value in load register 98. The alternate phase duration is given by the reference clock divided by the HOLD value in hold register 100. The total cycle period is the reference clock divided by the sum of the HOLD and LOAD values. Timer 90 is programmed so that its output pin toggles at the end of each phase to produce the desired pulse width modulated pulse train. In the illustrated embodiment, the LOAD value is used to control the duration of the high output state, while the HOLD value controls the duration of the low output state. Setting the DAC consists of storing the appropriate values in the load and hold registers 98, 100 such that the appropriate duty cycle is achieved and such that the LOAD plus HOLD sum (i.e., the total cycle time) remains constant.

In accordance with this construction, the duty cycle is then equal to:

DUTY =LOAD/(LOAD +HOLD)

The LOAD +HOLD constant is directly equal to the resolution of DAC 78. This is because the smallest change that can be made in DAC output is produced by adding or subtracting 1 to the LOAD value and doing the complementary operation to the HOLD value. It has been found empirically that many known ECL moieties can detect the individual steps in a synthesized ramp function if the resolution of the steps is more than 0.5 mV. over a wide range of a few volts. This requires a resolution of one LSB in a 16 bit binary number. Therefore, both load register 98 and hold register 100 are 16 bit registers.

In the illustrated embodiment, the clocking signal is 4.7727 MHz and the total time for each pulse cycle is set at 10 milliseconds. Therefore, a 16 bit counter can count up to at most 47,727 in 10ms, and the LOAD value and the HOLD value are each a maximum of 47,727. Integrator 96 is constructed to give a nominal ramping rate of ±4.77 volts/seconds when the pulse level is at ±2.5 volts, respectively.

Figure 4:
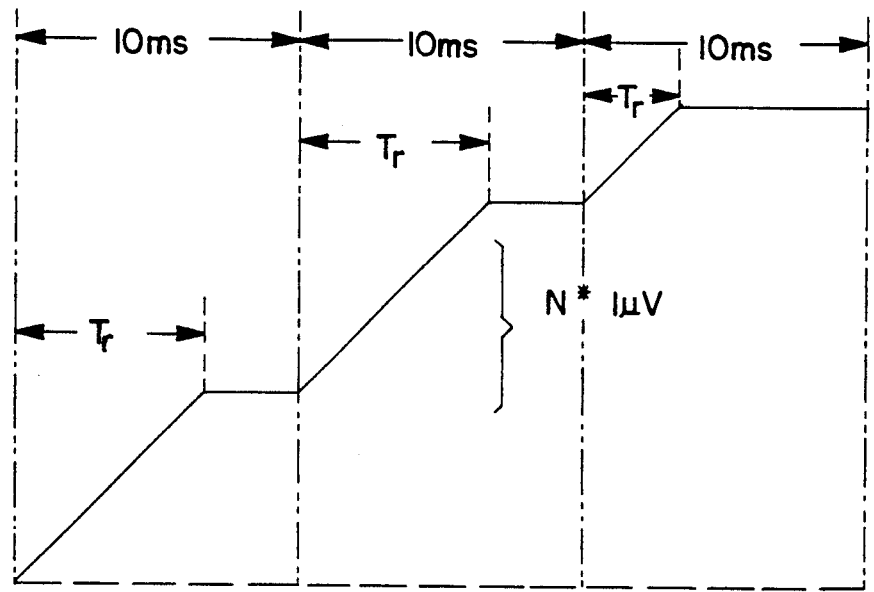
FIG. 4 is a waveform diagram of the voltage waveform produced by the pulse width modulated digital to analog converter of FIG. 3.

The output waveform produced by ramp DAC 78 is illustrated in FIG. 4 for an increasing ramp waveform. The integrator 96 accumulates voltage during the time period that the pulse is at its high +2.5 volt level for a period Tr. Tr may range from effectively 0 (when the LOAD value is at its smallest) to 10 milliseconds. These values give a range of duty cycle from 0% to 100%, and the effective overall ramping rate is therefore 477*Tr volts/seconds, with a resolution of 1 in 47,727, which is equal to 100uV/sec or 1uV/10ms cycle.

Figure 5:
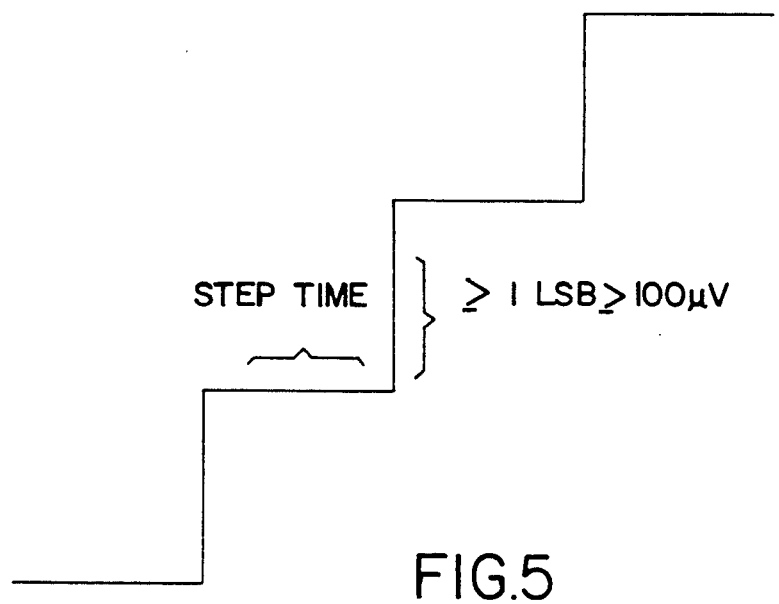
FIG. 5 is a waveform diagram of a conventional staircase ramp voltage waveform.

The ramp voltage waveform in FIG. 4 is to be compared with a conventional digitally generated staircase ramp function illustrated in FIG. 5. As shown therein, the conventional ramp staircase includes risers which have a minimum height of 1 LSB and a minimum step time which is fixed by the gating of the digital circuitry and can be very short. The resolution of the staircase function is therefore established by the resolution in the digital circuit producing the ramp staircase. Such a staircase ramp function can be digitally generated to a resolution of 1 in 16 bits using a 16 bit digital-to-analog converter. Such resolution is equivalent to 100uV. This resolution is 100 times worse than that achieved with Ramp Dac 78. Moreover, a 16 bit digital to analog converter is relatively expensive and presently costs approximately $400.00. A 16 bit 9513 timer chip, having five 9513 timers, on the other hand, costs about $22.00, and even when the cost of the switch 92, voltage reference sources 94 and integrator 96 are added in, the total cost for ramp DAC 78 is approximately $34.00. The remaining four timers on the chip may be used for other purposes, including other pulse width modulated DACs. When it is considered that apparatus 10 includes four such pulse width modulated DACs, it will be realized that the savings achieved in accordance with the present invention are dramatic. Furthermore, beyond the savings, the pulse width modulated Ramp Dac 78 in accordance with the present invention is superior to conventional 16 bit DACs, since the present pulse width modulated DACs have a resolution of almost one in 23 bits and alternate ramps with steps, as opposed to alternating rises with steps. Indeed, the integrator 96 smooths the transitions between the ramps and steps, which further adds to the overall smoothness of the synthesized ramp voltage waveform.

Figure 6:
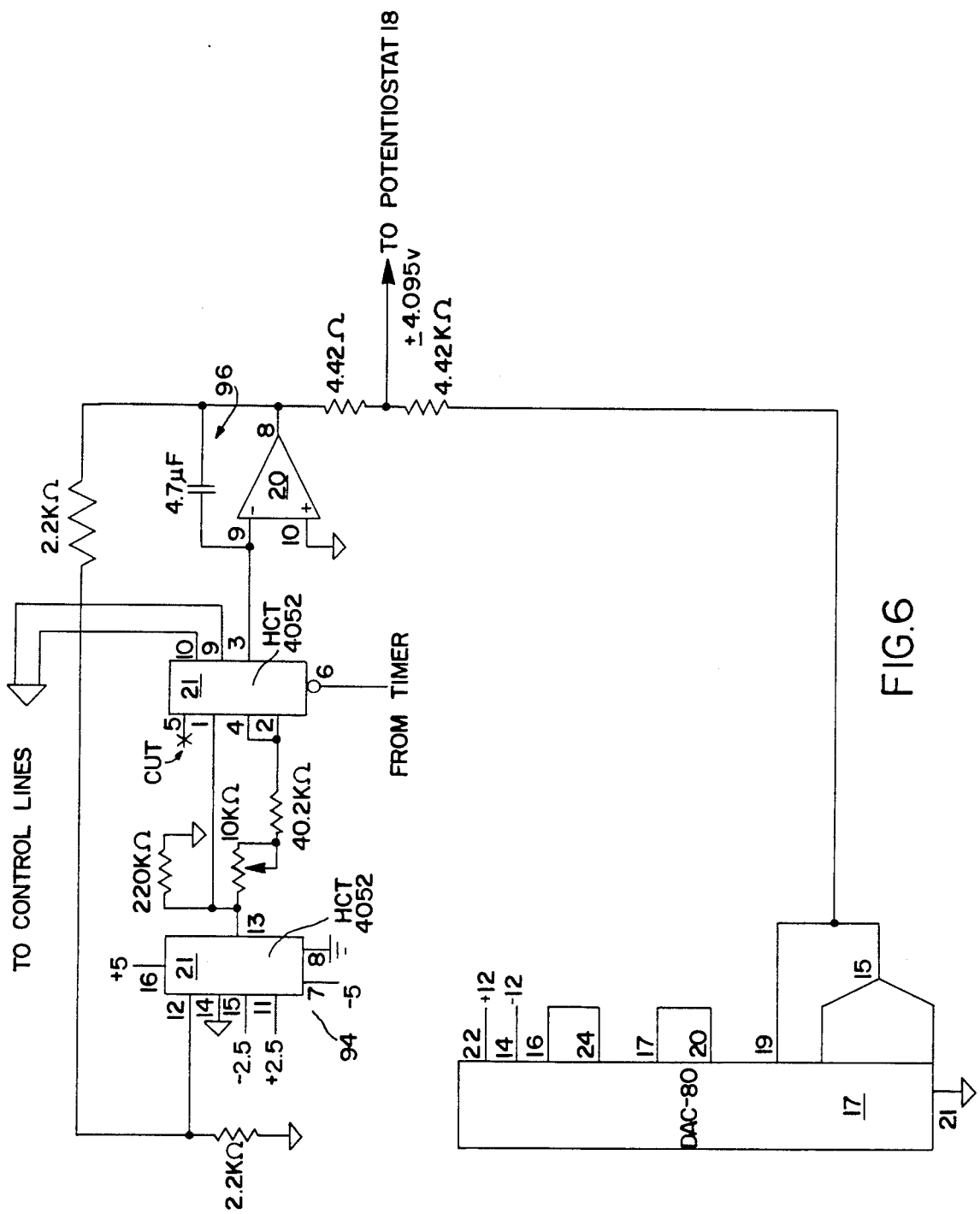
FIG. 6 is a block diagram of the pulse width modulated digital to analog converter of FIG. 3.
Figure 7A:
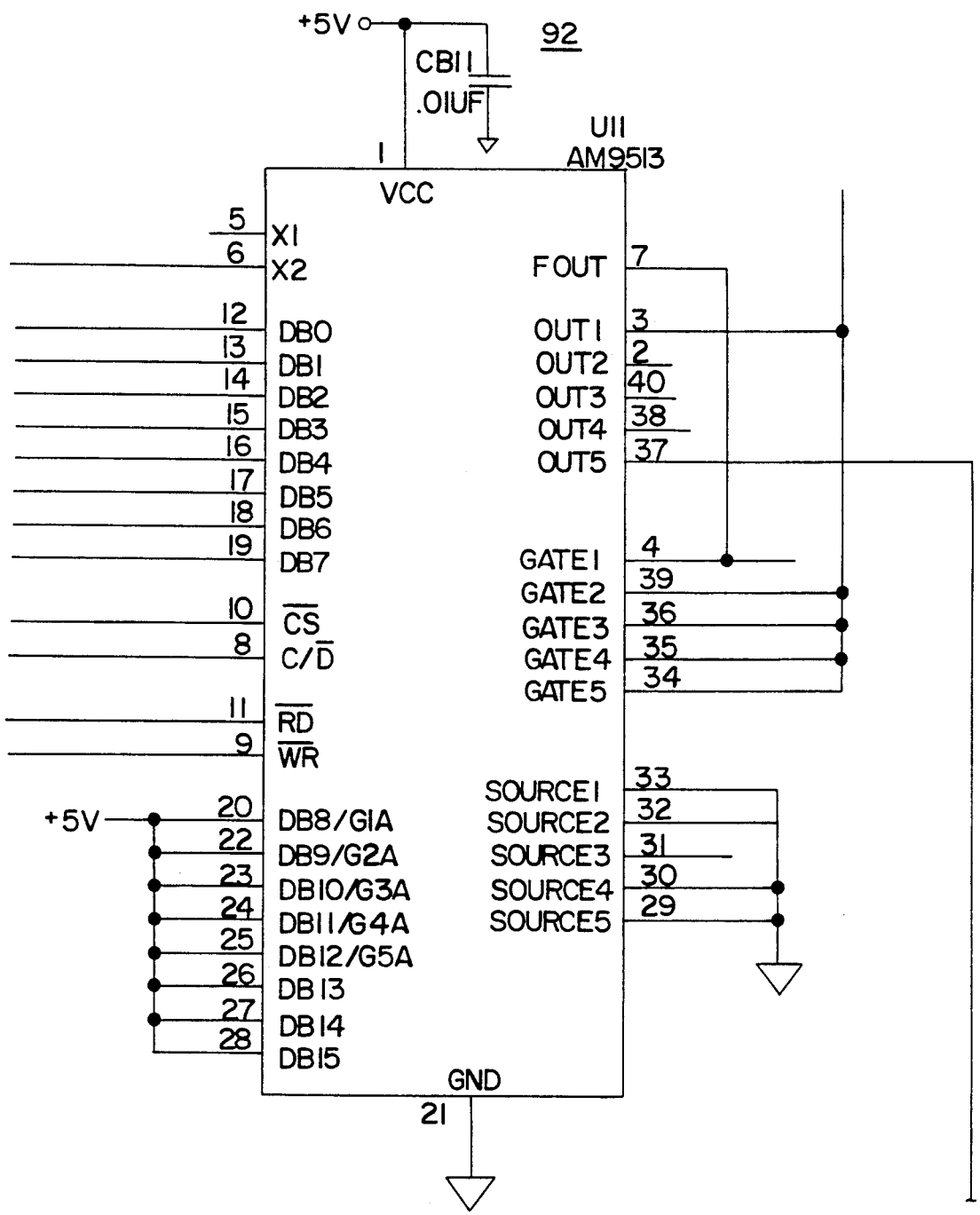
FIG. 7A and 7B together provide a wiring diagram of the pulse width modulated digital to analog converter of FIG. 3.
Figure 7B:
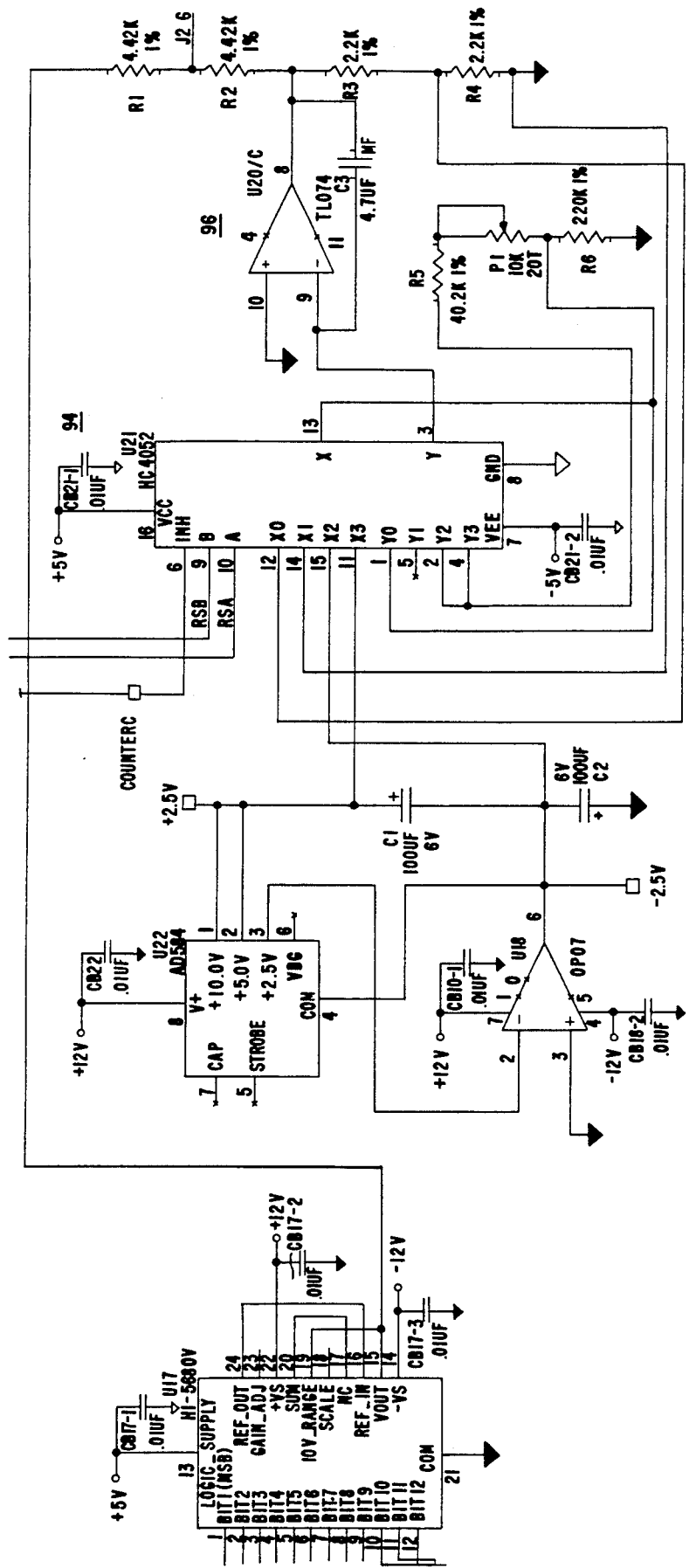

FIG. 6 is a block diagram of ramp DAC 78, while FIGS. 7A and 7B together provide a wiring diagram thereof.

In addition to ramp DAC 78, PMT HVDAC 58, luminosity output DAC 70 and auxiliary analog output DAC 72 are also pulse width modulated DACs in accordance with the present invention. The LOAD and HOLD values are adjusted for the particular function so that, for example, PMT HVDAC 58 has a LOAD +HOLD constant of 1500, corresponding to the reolution of 1 volt in the range of 0-1500 volts. However, since these three DACs 58, 70 and 72 are not intended to generate a ramp function, but rather to generate an analog value at a finely specified level, integrator 96 is omitted in each and in place thereof a low pass filter may be connected to attenuate any ac ripple in the output analog level.

Potential DAC is a conventional 12 bit DAC which is programmable in response to the second digital control signal to output the second voltage waveform as a series of one or more constant voltages.

The present invention has been described in connection with a single preferred embodiment, but it will be apparent to one of ordinary skill in the art that many changes and modifications may be made therein without departing from the spirit or scope of the present invention, which is to be determined from the appended claims.

What is claimed is:

1. Apparatus for conducting measurements of electrochemiluminescent phenomena, comprising:
   cell means for holding a sample fluid which contains an electrochemiluminescent moiety;
   detector means for detecting electromagnetic radiation emitted by said electrochemiluminescent moiety in said sample fluid and providing a signal indicative of the intensity of emitted radiation;
   control means for generating a digital control signal indicative of a selected slope of a ramp voltage waveform;
   digital to analog converter means for generating said ramp voltage waveform in response to said digital control signal; said digital to analog converter means comprising pulse width modulation means for converting said digital control signal to a pulse width modulated control signal; and integrator means for producing said ramp voltage waveform whose slope is determined by said pulse width modulated control signal produced by said pulse width modulation means; and
   means for supplying electrochemical energy to said sample fluid in response to the ramp voltage waveform such that said electrochemiluminescent moiety in said sample fluid is induced to repeatedly emit electromagnetic radiation.

2. Apparatus according to claim 1 wherein said control means comprises means for generating a second digital control signal indicative of a second voltage waveform composed of at least one constant voltage, said apparatus further comprising second digital-to-analog converter means for generating said second voltage waveform in response to said second digital control signal, and wherein the means for supplying electrochemical energy to said sample fluid in response to the ramp voltage waveform comprises means for supplying electrochemical energy to said sample fluid in response to the second voltage waveform.

3. Apparatus according to claim 1 further comprising fluid transport means for transporting said sample fluid to and from said cell means.

4. Apparatus according to claim 1 wherein said control means includes programmable digital computing means for generating said digital control signal.

5. Apparatus according to claim 1 wherein said pulse width modulation means includes programmable timer means for providing a first pulse width modulated pulse train in response to the digital control signal indicative of said selected slope of said ramp voltage waveform;
   first and second voltage sources defining upper and lower pulse amplitudes, respectively; and
   multiplexer means connected to said first and second voltage sources and responsive to said first pulse width modulated pulse train for producing said pulse width modulated control signal as a second pulse width modulated pulse train having at least one of said upper and lower pulse amplitudes.

6. Apparatus according to claim 5 wherein said control means is operative to supply said digital control signal having load values and hold values and wherein said programmable timer means includes sixteen bit counter means including a sixteen bit load register and a sixteen bit hold register for holding said load and hold values, respectively, the duty cycle of each pulse within said first pulse width modulated pulse train being equal to said load value divided by the sum of said load and hold values, whereby the resolution of said digital to analog converter means is greater than sixteen bits.

7. Apparatus according to claim 1 wherein said detector means includes light detector means for detecting photons of said electromagnetic radiation emitted by said electrochemiluminescent moiety in said sample fluid and providing an output pulse in response to each detected photon, and counter means responsive to said output pulses for providing said signal indicative of the intensity of emitted radiation.

8. Apparatus according to claim 7 wherein said signal indicative of the intensity of emitted radiation is a digital signal.

9. Apparatus according to claim 7 wherein said light detector means includes photomultiplier tube means.

10. Apparatus according to claim 7 wherein said counter means provides a first digital signal indicative of a count of a first fractional number of said output pulses and a second digital signal indicative of a count of a second fractional number of said output pulses.

11. Apparatus according to claim 10 further comprising output digital to analog converter means for converting a selected one of said first and second output digital signals to analog form.

12. Apparatus for conducting measurements of electrochemiluminescent phenoma, comprising:
cell means for holding a sample fluid which contains an electrochemiluminescent moiety;
means for introducing a sample fluid containing an electrochemiluminescent moiety to said cell means;
detector means for detecting electromagnetic radiation emitted by said electrochemiluminescent moiety in said sample fluid and providing a signal indicative of the intensity of emitted radiation;
ramp voltage generating means for generating a ramp voltage waveform having a selected slope, said ramp voltage generating means including means for producing a control signal representing said selected slope, and means for producing said ramp voltage waveform having said selected slope in response to said control signal; and
means for supplying electrochemical energy to said sample fluid in response to the ramp voltage waveform said that said electrochemiluminescent moiety in said sample fluid is induced to repeatedly emit electromagnetic radiation.

13. An apparatus as recited in claim 12 wherein said means for introducing a sample fluid to said cell means includes fluid transport means for introducing a sample to and from said cell means.

14. Apparatus for conducting measurements of electrochemiluminescent phenomena, comprising:
cell means for holding a sample fluid which contains an electrochemiluminescent moiety;
detector means for detecting electromagnetic radiation emitted by said electrochemiluminescent moiety in said sample fluid and providing a signal indicative of the intensity of emitted radiation;
computer control means for generating a first predetermined voltage waveform having at least one selected slope; said computer control means including means for producing a control signal representing said selected slope, and means for producing said first predetermined voltage waveform having said selected slope in response to said control signal; and
means for supplying electrochemical energy to said sample fluid in response to the first predetermined voltage waveform such that said electrochemiluminescent moiety in said sample fluid is induced to repeatedly emit electromagnetic radiation.

15. An apparatus as recited in claim 14 wherein said computer control means comprises means for generating a ramp voltage waveform as said first predetermined voltage waveform.

16. An apparatus as recited in claim 14 wherein said computer control means comprises means for generating a curved waveform as said first predetermined voltage waveform.

17. An apparatus as recited in claim 16 wherein said means for generating a curved waveform comprises means for generating a sinusoidal waveform.

18. An apparatus as recited in claim 15 wherein said computer control means comprises means for generating a second predetermined voltage waveform, and means for combining said ramp voltage waveform and said second predetermined voltage waveform.

19. An apparatus as recited in claim 12, wherein said means for producing a control signal comprises means for producing a digital control signal representing said selected slope, and wherein said means for producing said ramp voltage waveform comprises means for producing said ramp voltage waveform having said selected slope in response to said digital control signal.

20. An apparatus as recited in claim 19, wherein said means for producing said ramp voltage waveform comprises means for producing a pulse train which is pulse width modulated in response to the digital control signal, and means for integrating said pulse train to produce said ramp voltage waveform.

21. An apparatus as recited in claim 14, wherein said means for producing a control signal representing said selected slope comprises computer means for producing a digital control signal representing said at least one selected slope; and wherein said means for producing said first predetermined voltage waveform comprises means for producing said predetermined voltage waveform having said selected slope in response to said digital control signal.

22. An apparatus as recited in claim 21, wherein said means for producing said first predetermined voltage waveform comprises integrator means for producing said first predetermined voltage waveform in response to a control input signal supplied thereto representing said selected slope of said first predetermined voltage waveform; and means for supplying said control input signal to said integrator means in response to said digital control signal such that said integrator means produces said first predetermined voltage waveform having said selected slope.

* * * * *